United States Patent [19]

Martin

[11] Patent Number: 5,741,281
[45] Date of Patent: Apr. 21, 1998

[54] SUTURE SECURING APPARATUS

[75] Inventor: Christopher Martin, New South Wales, Australia

[73] Assignee: Smith & Nephew, Inc., Andover, Mass.

[21] Appl. No.: 643,855

[22] Filed: May 7, 1996

Related U.S. Application Data

[63] Continuation of Ser. No. 97,694, Jul. 27, 1993, abandoned.

[51] Int. Cl.⁶ ..................................... A61B 17/00
[52] U.S. Cl. .................. 606/148; 606/139; 606/144; 606/151
[58] Field of Search ..................... 606/139, 144, 606/142, 143, 145, 148, 151, 205, 207, 232

[56] References Cited

U.S. PATENT DOCUMENTS

| | | | |
|---|---|---|---|
| 2,277,139 | 3/1942 | Niemand | 606/143 |
| 3,364,933 | 1/1968 | Leopold | 606/207 |
| 3,409,014 | 11/1968 | Shannon | |
| 3,541,591 | 11/1970 | Hoegerman | |
| 3,664,345 | 5/1972 | Dabbs et al. | |
| 3,665,926 | 5/1972 | Flores | 606/144 |
| 3,687,138 | 8/1972 | Jarvik | |
| 3,763,860 | 10/1973 | Clarke | |
| 3,802,438 | 4/1974 | Wolvek | |
| 3,877,434 | 4/1975 | Ferguson et al. | 606/139 |
| 3,880,166 | 4/1975 | Fogarty | |
| 3,910,281 | 10/1975 | Kletscka et al. | |
| 3,976,079 | 8/1976 | Samuels et al. | |
| 4,177,813 | 12/1979 | Miller et al. | 606/139 |
| 4,235,238 | 11/1980 | Ogiu et al. | |
| 4,291,698 | 9/1981 | Fuchs et al. | |
| 4,409,974 | 10/1983 | Freeland | |
| 4,592,355 | 6/1986 | Antebi | 606/144 |
| 4,741,330 | 5/1988 | Hayhurst | |
| 4,750,492 | 6/1988 | Jacobs | |
| 4,932,962 | 6/1990 | Yoon et al. | |
| 4,961,741 | 10/1990 | Hayhurst | |
| 4,968,315 | 11/1990 | Gatturna | 606/232 |
| 5,021,059 | 6/1991 | Kensey et al. | |
| 5,037,433 | 8/1991 | Wilk et al. | 606/139 |
| 5,078,731 | 1/1992 | Hayhurst | |
| 5,084,058 | 1/1992 | Li | |
| 5,129,912 | 7/1992 | Noda et al. | |
| 5,144,961 | 9/1992 | Chen et al. | |
| 5,160,339 | 11/1992 | Chen et al. | |
| 5,171,251 | 12/1992 | Bregen et al. | |
| 5,192,287 | 3/1993 | Fournier et al. | |
| 5,196,022 | 3/1993 | Bilweis | 606/139 |
| 5,217,471 | 6/1993 | Burkhart | |
| 5,236,434 | 8/1993 | Callicrate | 606/139 |
| 5,284,485 | 2/1994 | Kammerer et al. | 606/148 |
| 5,312,423 | 5/1994 | Rosenbluth et al. | 606/148 |

FOREIGN PATENT DOCUMENTS

| | | | |
|---|---|---|---|
| 0 492 172 A1 | 7/1992 | European Pat. Off. | |
| WO 93/02625 | 2/1993 | WIPO | A61B 17/00 |

*Primary Examiner*—Jeffrey A. Schmidt
*Attorney, Agent, or Firm*—Fish & Richardson P.C.

[57] ABSTRACT

A suture securing apparatus for positioning a suture securing device having a passage therethrough. The apparatus includes a holding member having at one end a handle and at the other end means for engaging a suture securing device, a suture recovery member adapted to draw a loop of suture through the passage in the suture securing device, and a suture clamping element adapted to securely engage suture which has been passed through the loop in the suture securing device.

22 Claims, 7 Drawing Sheets

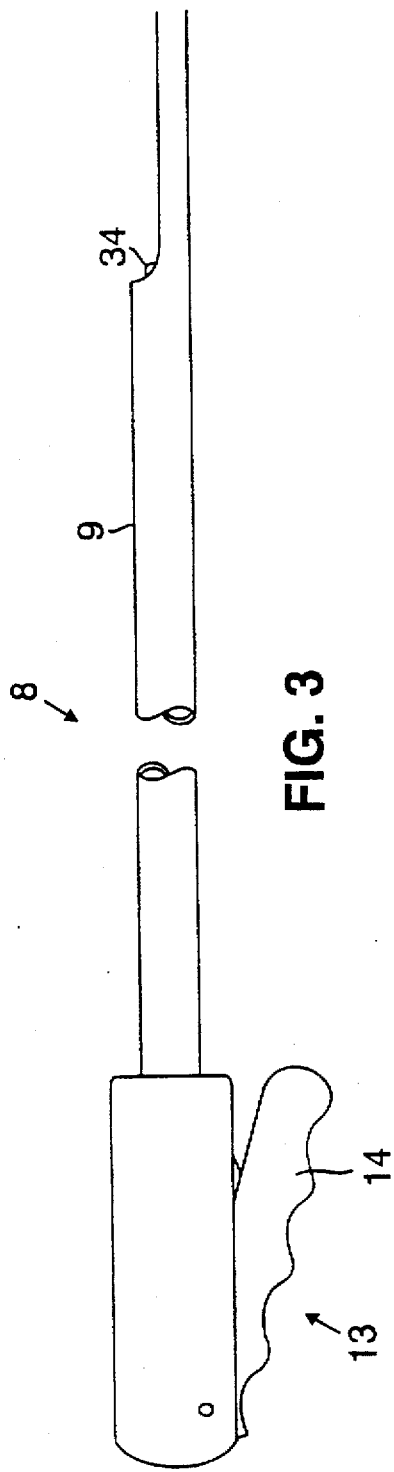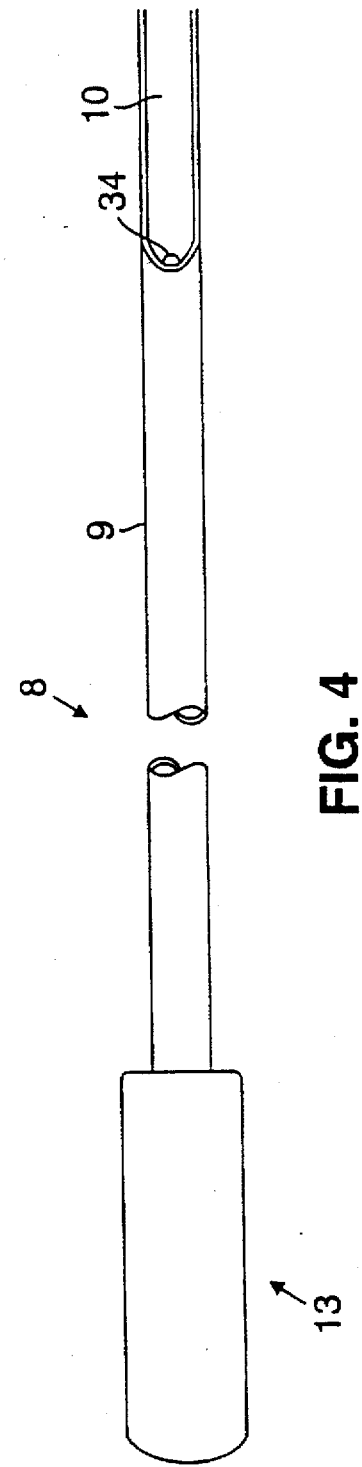

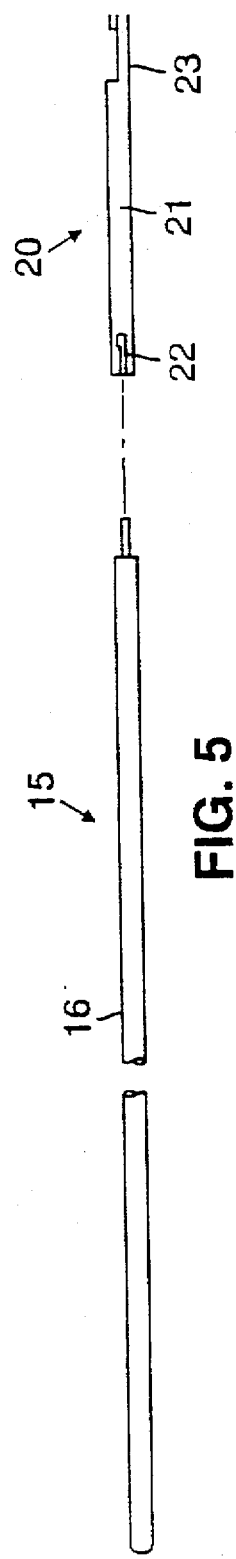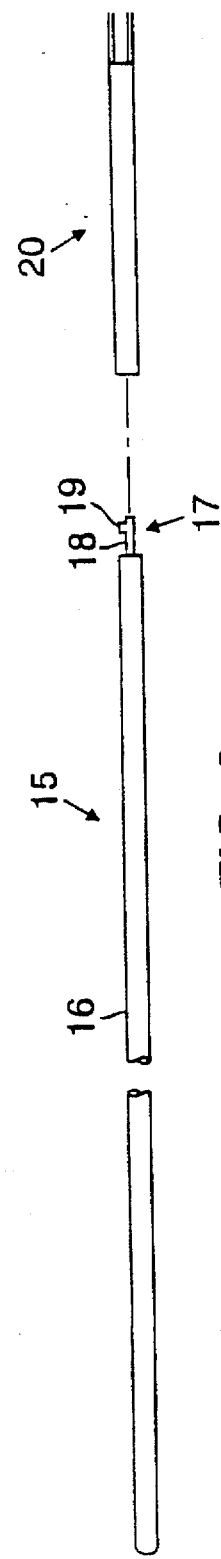

SUTURE SECURING APPARATUS

CROSS REFERENCE TO RELATED APPLICATIONS

This is a continuation of application Ser. No. 08/097,694, filed Jul. 27, 1993, now abandoned.

The present invention relates generally to surgical instruments, more particularly it relates to a novel suture securing apparatus. It will be convenient to hereinafter refer to the suture securing apparatus in relation to endoscopic surgery however it should be noted that the invention has a wider application.

The basic principles of surgery are incision, dissection, traction, counter-traction, ligation and suturing. These principles are well established and mastered in conventional "open" invasive surgical procedures where access to the surgical site is gained by incision through the patient's skin and body wall to expose the site. In recent times attention has been directed towards least invasive surgical procedures or non-invasive procedures such as endoscopy, which encompasses arthroscopy, laparoscopy, duodenoscopy, gastroscopy and the like, where access to the surgical site is gained by introducing surgical instruments down one or more portals and/or gastrointestinal tract from the mouth or anus and/or urinary tract via the urethra. Least invasive surgery, where possible, has many benefits over conventional invasive procedures such as reduced surgical trauma, lessened anaesthesis and shortened recovery times, leading to reduced hospital costs, greater patient comfort and earlier return to work.

Although some of the technology for laparoscopic surgery has been available for many years, the first laparoscopic cholecystactomy performed in 1987 has stimulated the interest of general surgeons in laparoscopic surgery. Many general surgeons have transferred the basic principles of surgery to laparoscopic and endoscopic surgery and have mastered with reasonable ease these principles with the exception of suturing. In endoscopic procedures difficulty arises in tying of a suture as the surgeon can only use instruments to manipulate the required knots. Manipulation of the suture is hindered as usually the surgeon has only a two dimensional viewing field—the suture site being visible by use of a camera and television screen or specialized scope. The problem of suturing and especially tying knots during laparoscopic surgery has become more apparent as surgeons have moved from resectional surgery i.e. where part of an organ or tissue is completely or partially removed such as cholecystectomy or appendectomy, to surgery which requires suture placement such as procedures of fundoplication, bowel resection etc. Resectional procedures such as cholecystectomy and appendectomy generally only require ligature or clip application to tie off the removed organ or blood vessel. Devices have been developed to facilitate intracorporeal placement of such clips or ligatures and the application of such ligatures or clips is relatively simple when compared to tying of intracorporeal knots in sutures. At the present time the average surgeon is not confronted with the need for intracorporeal knot tying frequency enough to become adapt at this skill and this may contribute to longer operating times. Considerable time and practice may be required before a surgeon becomes skilled at tying of knots during endoscopic surgery.

A method for tying knots extracorporeally has been developed where the slip knot is tied in the suture outside the body of the patient and then positioned at the desired site by means of a push-rod into the body. While this method is successful to some extent it suffers from a number of disadvantages. Many endoscopic procedures involve the inflation of a body cavity with a pressurized gas such as carbon dioxide so that a space is created in the body to make the surgical site visible. The gas pressure is kept constant to maintain the visual field and if the pressure is reduced by the escape of gas the visual field is lost or impaired as the body tissues resume their usual positions. In tying a knot in a suture outside the body it is necessary to pass the knot beyond a seal established to create the internal gas space. This involves breaking of the gas seal and the temporary loss of the gas space and hence the visual field as gas escapes when the suture is being passed into the body.

Secondly, the extracorporeally tied knots are not always as secure as would be desirable and thus present the risk of failure.

Thirdly, extracorporeally tied knots are not always satisfactory for securing opposite ends of a suture which closes an elongate wound.

The applicant has described a novel device for securing a suture in co-pending Australian Application No. PL 5843, the entire contents of which are herein incorporated by reference. The novel suture securing device comprises:

a surgically implantable body having a tissue abutting side and a suture loop side; and passage through said body, the passage having an opening adjacent the tissue abutting side and another opening adjacent the suture loop side.

In order to facilitate positioning of such a suture securing device it is desirable to provide apparatus which can engage such device and assist in tying a suture about the device, and then assist in moving the device along the suture to the desired position.

Accordingly it is an object of the present invention to provide a suture securing apparatus suitable for holding a suture securing device, assisting in tying a suture about said device end positioning said device.

It is another object of the invention to provide an apparatus which can be utilized in endoscopic surgery to perform the functions of holding, tying and positioning a suture securing device.

It is yet another object of the invention to provide apparatus which can be used in endoscopic surgery to perform the abovementioned functions without the need for removal of the apparatus from the operating site.

It is still another object of the invention to provide an attachment to a suture securing apparatus which has a suture securing device pre-loaded thereon to allow rapid tying of a suture.

It is another object of the invention to provide a method for adjustment of a suture securing device using a suture securing apparatus.

Other objects and advantages of the invention will become apparent from the following description.

In one aspect of the invention there is provided suture securing apparatus for positioning a suture securing device having a passage therethrough, the apparatus comprising:

(i) holding member having at one end a handle means and at the other end means for engaging said suture securing device;

(ii) suture recovery means adapted to draw a loop of suture through the passage in said securing device; and (iii) suture clamping means adapted to securely engage suture which has been passed through the loop in said suture securing device.

In one aspect of the invention the apparatus must be capable of holding a suture securing device, drawing a loop of suture through the passage in the securing device and grasping a suture. In one embodiment, suture clamping means may comprise two cooperating members, one member having a loop with an abutment portion and the other member comprising a tongue adapted to bear upon the abutment portion such that when a suture is passed through the loop, such the tongue is brought to bear against the abutment surface, the suture is securely held between the tongue and abutment portion.

Suture recovery means may be any suitable means for drawing a suture through the passage in the suture securing device. In a preferred embodiment the suture recovery means comprises an elongate member having a loop at one end said loop being passable through the passage in the suture securing device whereupon the suture can be passed through the loop and the loop then withdrawn through the passage bringing a loop of suture therewith. The suture recovery means must then be capable of being disengaged from the loop of suture drawn through the securing device. In one embodiment the suture recovery means is a flexible wire which can be passed down a passage in the apparatus. In another embodiment suture recovery means includes a securable thread attached to a disposable member attachable to a shaft, the thread being frangibly attached to the shaft. In one embodiment the suture recovery means is automated to load the loop of suture and sever the thread in one action by actuating a lever or the like.

The holding member has at one end a handle for manipulation of the apparatus by a surgeon. The other end of the holding member has means for engaging a suture securing device. Said means for engaging the suture securing device may be any suitable means to firmly hold the securing device whilst being positioned proximate the suture site and which can then disengage the suture securing device when desired. In one embodiment, means for engaging the suture securing device comprise two or more tines, portions of which engage corresponding recesses in each end of the suture securing device. Each tine may include projecting members adapted to locate corresponding recesses in the suture securing device.

In a further embodiment of the invention the apparatus consists of an elongate body having a manipulating end and a device holding end, the device holding end having at least two tines with device engaging portions resiliently biased towards one another, and means for forcing said device engaging portions away from each other. In one embodiment the means for forcing the device engaging portions apart consist of a ram, which preferably extends from the manipulating end to the device holding end of the apparatus, which acts upon came located on the tines. When the ram contacts the cams, the tines and hence the device engaging portions are forced apart to release the device held thereby. Preferably the ram is actuated by a plunger, or other suitable means at the manipulating end of the apparatus. In this embodiment the apparatus may be provided in combination with integral suture recovery means and/or suture clamping means, or without said suture recovery means and/or suture clamping means.

It will now be convenient to describe the invention in more detail with reference to a preferred embodiment illustrated in the accompanying drawings. It is to be understood that the drawings and the following description relate to a preferred embodiment only, and not intended to limit the scope of the present invention.

FIG. 3 is a side elevation of a suture clamping means of the present invention.

FIG. 4 is a plan view of a suture clamping means of FIG. 3.

FIG. 5 is a plan of a suture recovery means incorporating a separate suture loading member.

FIG. 6 is a side elevation of the suture recovery means of FIG. 5.

Figure 1:
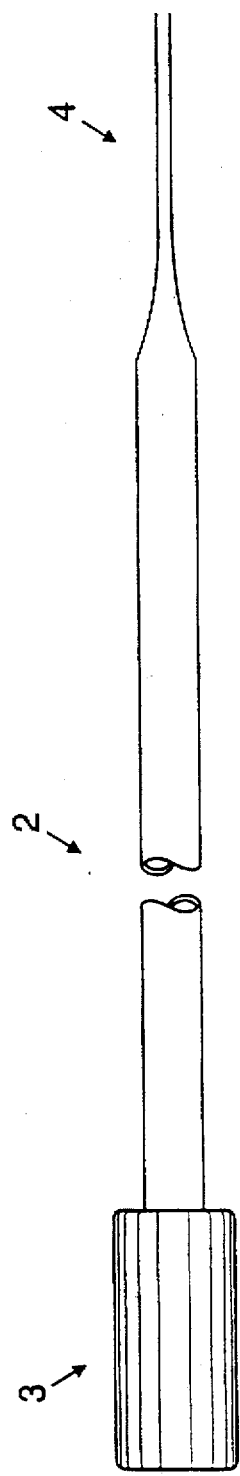
FIG. 1 is a side elevation of a member for holding a suture securing device.
Figure 2:
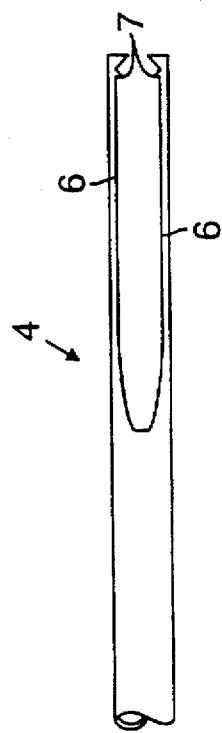
FIG. 2 is a plan of portion of the member of FIG. 1 which holds the suture securing device.
Figure 7:
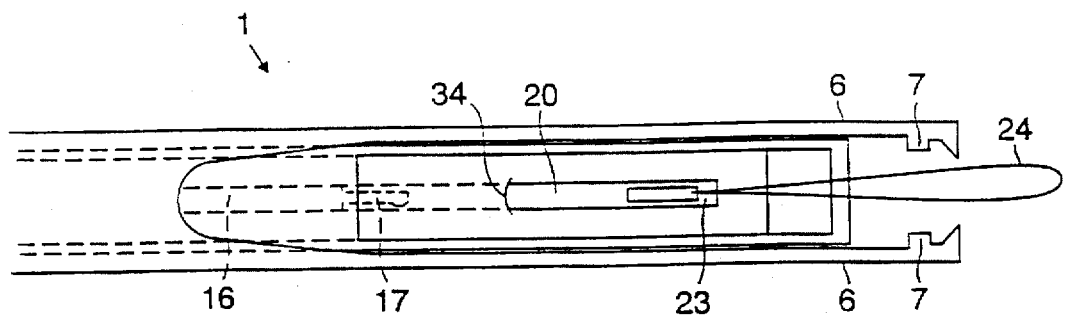
FIG. 7 is a plan view of the part of a suture securing apparatus which ties the suture about a suture securing device in assembled form.

Apparatus 1 comprises a holding member 2 having at one end a handle 3. Handle 3 is configured to allow a surgeon to easily manipulate apparatus 1 during surgery. At the other end of elongated member 2 there is provided device holding means 4 adapted to hold a suture securing device 5. Device holding means 4 may comprise a plurality of tines 6 having projecting members 7 adapted to locate in corresponding recesses in device 5. Preferably, holding member 2 is suitably configured for use in endoscopic surgery i.e. device holding means and at least a portion of elongate member 2 is capable of being passed down a portal to the desired operating site. Tines 6 and projecting members 7 should be capable of firmly holding a suture securing device 5 but such that after device 5 has been placed at a desired position, device holding means 4 can be disengaged from device 5. Tines 6 may be resiliently biased towards a position where they firmly engage a suture securing device 5 positioned therebetween.

Figure 14:
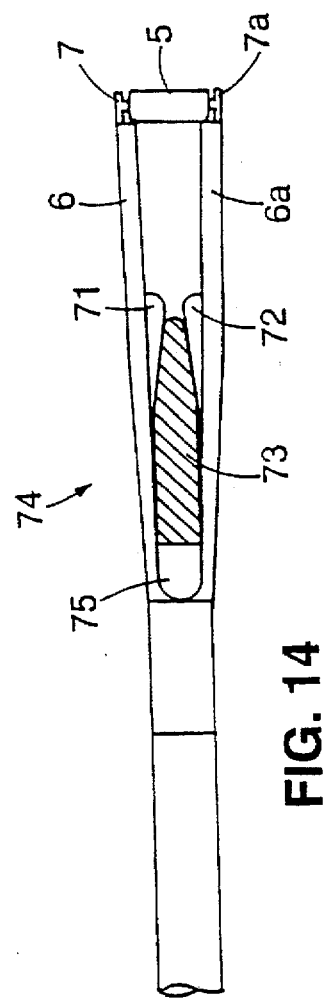
FIG. 14 is a plan view of the apparatus in FIG. 13 with the device released.
Figure 15:
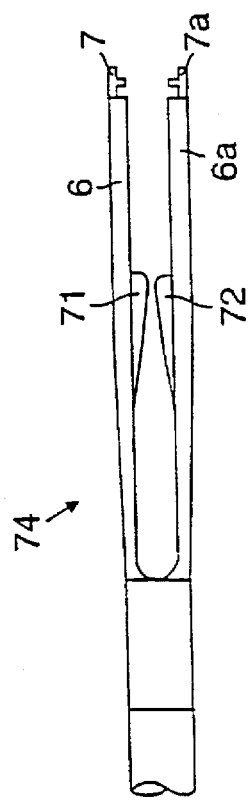
FIG. 15 is a plan view of the apparatus with the ram retracted.
Figure 16:
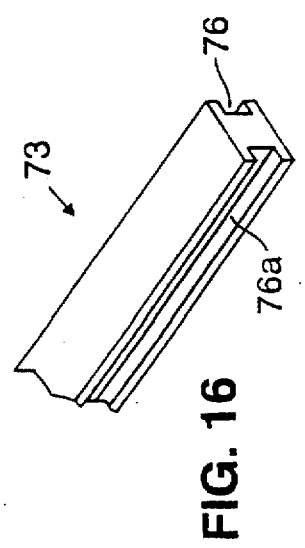
FIG. 16 is a perspective view of a portion of the ram showing its end section.

In the embodiment of the invention shown in FIGS. 13, 14, 15 and 16 tines 6 and 6a carry cams 71 and 72 which interact with ram 73 at the device holding end 74 of a shaft 75. When a plunger or other actuating means at the manipulation end (not shown) of the apparatus is actuated, force is transmitted along shaft 75 to drive ram 73 onto cams 71 and 72 as shown in FIG. 14. Tines 71 and 72 and hence projecting members 7 and 7a are formed apart to disengage from corresponding recesses in device 5. Ram 73 is shown sectioned in FIGS. 13 and 14. Ram 73 has cam grooves 76 and 76a such that ram 73 positively engages camp 71 and 72 when actuated.

In the first embodiment of the invention apparatus 1 further comprises suture clamping means 8. In a preferred embodiment, clamping means 8 consists of two cooperating members 9 and 10 which act in concert to grasp and firmly hold a suture which has been passed between clamp faces 11 and 12. In one embodiment, cooperating member 10 may be accommodated in an axial bore through member 9. Clamp face 11 may be a tongue on member 10 adapted to bear upon clamp face 12 of member 9. Suture clamping means 8 further includes an actuating mechanism 13 and capable of moving clamp faces 11 and 12 relative to each other such that a suture passed between faces 11 and 12 can be clamped. Actuating mechanism 13 may be a lever 14, which when depressed by the surgeon moves cooperating members 9 and 10 relative to each other and brings clamp faces 11 and 12 together. In a preferred embodiment, suture clamping means 8 is located in an axial bore through elongate member 2.

Apparatus 1 further comprises suture recovery means 15 adapted to draw a loop of suture through a passage in device 5. Suture recovery means may be a thread or wire passing along apparatus 1 and which forms a loop proximate tines 6 and which passes out of the handle 3 and actuating mechanism 13 of apparatus 1. In a preferred embodiment, suture recovery means 15 consists of a shaft 16 which passes along apparatus 1 and emerges from the apparatus 1 adjacent to actuating mechanism 13. At the other end of shaft 16 there is provided a coupling means 17 consisting of a finger 18 which projects from the end of shaft 16 and a stud 19 positioned on finger 18. Suture loading member 20 consists of a body 21 locatable within a bore (not shown) and having shaft coupling means 22 adapted to releaseably engage with coupling means 17. Shaft coupling means 22 may be a recess adapted to receive coupling means 17. Coupling means 17 may also be located on loading member 20 (not shown) and corresponding shaft coupling means 22 may be located on the end of shaft 16 (not shown). Body 21 includes a head portion 23, a frangible loading loop 24 attached to head portion 23 such that when body 21 and head portion 23 are retracted into the bore, loading loop 24 is severed. Loading loop 24 may be severed by a scissor action between the head portion 23 and an incising edge 34 at bore opening of suture clamping means 8. Preferably suture recovery means 15 is configured such that shaft 16 cannot be fully retracted from apparatus 1 during tying and stops such that the tip of head portion 3 is retained within the bore such that the gas seal is not broken. Loading loop may be any suitable flexible material capable of drawing a suture through a passage in securing device 5. Loading loop 24 may itself be made from suture material.

To position a suture securing device 5 at a desired surgical site, the following procedure may be adopted. Where a single suture securing device 5 is desired to secure a suture the device may be of the kind shown in FIG. 8 having one end of the suture 26 securely affixed thereto and emerging from said device adjacent a tissue abutting face 27. The free end 28 of the suture terminates in a suturing needle 29. In a preferred embodiment, suture securing device 5 is provided with suture 26 pre-attached and with loading loop 24 pre-positioned through passage 30 of device 5. The head 31 of loading loop 24 emerges from passage 30 one the tissue abutting side 27 of device 5. The end of loading loop 24 on the opposite side of device 5 is affixed to the head portion 23 of suture loading member 20. Pre-loaded suture securing device 5 with suture loading member 20 is introduced into the body of the patient and shaft coupling means 22 is connected to coupling means 17 on suture recovering means 15 by inserting finger 18 into shaft coupling means 22 and then rotating shaft 16 such that stud 19 engages in shaft coupling means 22. Suture securing device 5 is then manipulated between tines 16 until projecting members 7 locate in corresponding recesses in suture securing device 5. Tissue abutting face 27 of device 5 faces away from apparatus 1 towards the surgical site. Suturing can then commence as desired.

Figure 8:
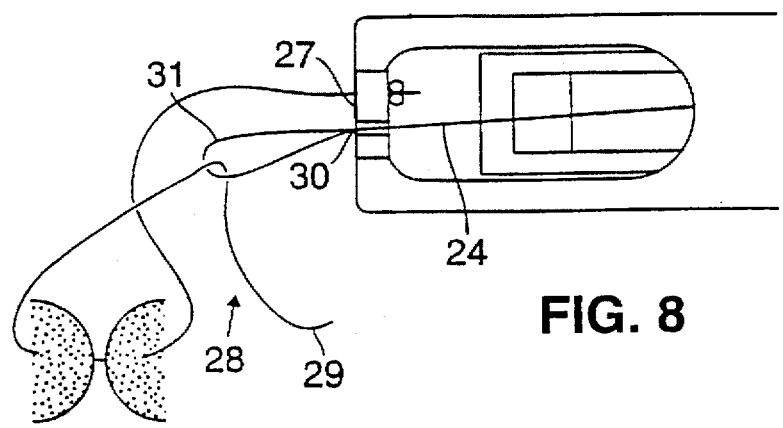
FIGS. 8 to 12 are plan views of a suture securing apparatus of the invention at various stages of securing of a suture securing device.
Figure 9:
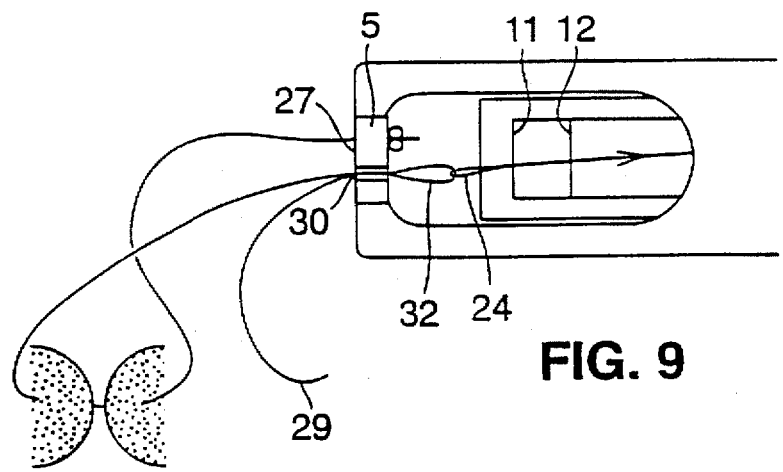

Once suturing has been completed needle 29 is then passed through the head 31 of loading loop 24 as shown in FIG. 8. Suture 26 is then drawn through passage 30 as shown in FIG. 9 by retracting suture recovery means until a loop of suture 32 emerges on the apparatus side of device 5. Preferably, loop of suture 32 is drawn until it is adjacent with clamp faces 11 and 12. Further retraction of suture recovery means 15 brings head portion 23 of loading member 20 past an edge 34 of the bore in which suture recovery means 15 is located. By drawing head portion 23 past such point, edge 34 severs a part of loading loop 24 so that loading loop 24 and suture loop 32 become disengaged. Suture loading member with loading loop 24 can then be removed from the opening site as desired.

Figure 10:
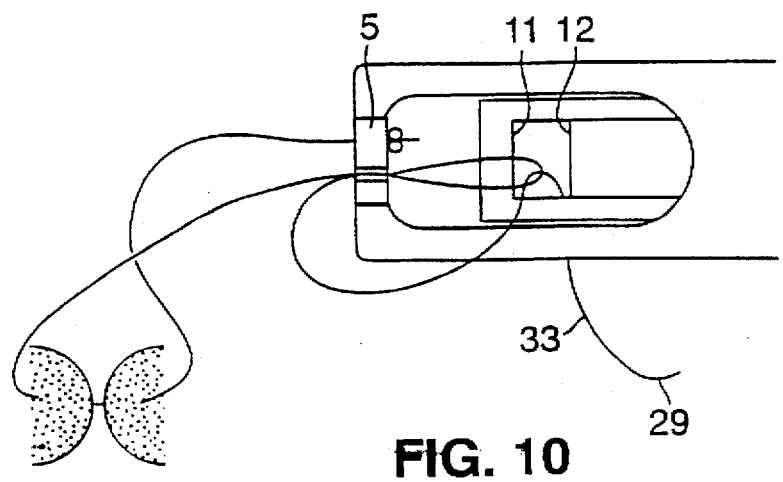
Figure 11:
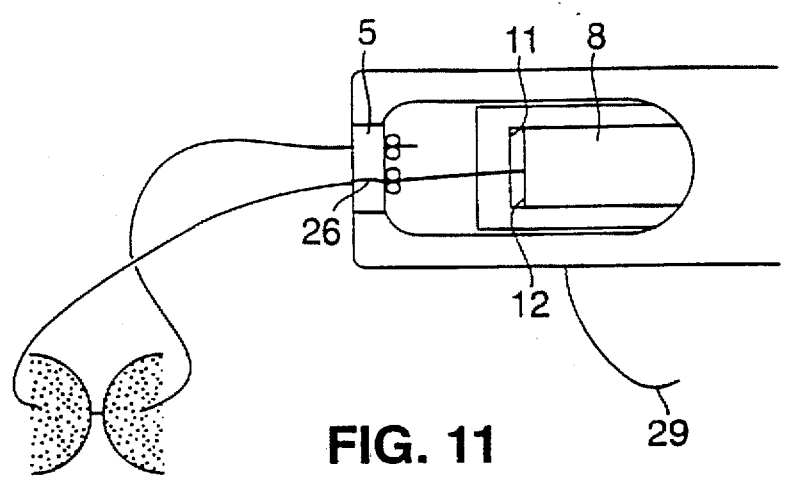
Figure 12:
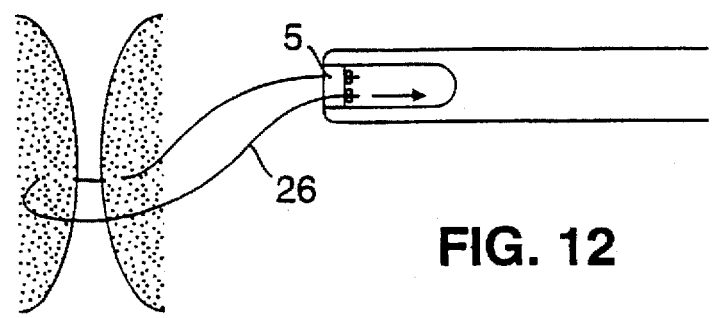
Figure 13:
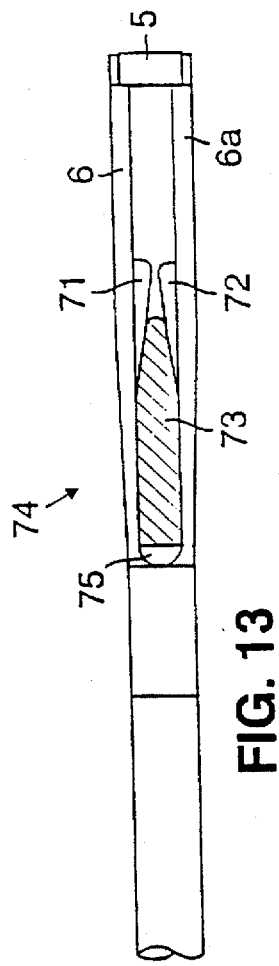
FIG. 13 is a plan view of an apparatus of the present invention shown holding a suture securing device.

Needle 29 and adjacent portion of suture 33 is then passed through suture loop 32 and between clamp faces 11 and 12 as shown in FIG. 10. By actuating mechanism 13 through lever 14, clamp faces 11 and 12 are brought together to clamp the suture as shown in FIG. 11. Suture clamping means 8 may then be retracted relative to device 5 to tension suture 26, as shown in FIG. 11. Finally, in order to position suture securing device 5 at the desired site, holding member 2 is pushed towards the desired site whilst suture clamping means 8 draws slack suture through device 5. As the suture can only be pulled one way through device 5, the device can be manipulated towards the tissue against which it is to hold the suture 26. Once at the desired site, elongate member 2 can be retracted and the secure hold of device 5 enables tines 6 to release the device when retracted. Excess suture material can then be severed.

If the suture securing device 5 is to secure only one end of suture 26, the device need not be provided with the pre-attached suture as previously described. The suture securing device 5 need only be provided with one bore.

The apparatus 1 may further be utilized to position a suture securing device 5 for ligation of a vessel, organ, duct, tissue or the like. A suture securing device 5 may be provided pre-tied with a suture and loaded into apparatus 1 in the form shown in FIG. 11. The suture 26 need not be provided with a needle 29. The loop of suture emerging from the tissue abutting side of the device 5 may simply be slipped around the tissue, vessel, organ, duct or the like in a lasso fashion, rather than being passed through the tissue as shown in FIG. 11. The device 5 may be positioned to ligate the desired site in a manner identical to that described above, i.e. by clamping the free end of the suture between clamp faces 11 and 12, by pushing holding member 2 and device 5 towards the desired site whilst suture clamping means 8 draws suture through device until tightened adequately.

Preferably, suture recovery means 15 and suture clamping means 8 are located within axial bores in elongate member 2 so that device holding 4, clamp faces 11 and 12 and loading loop 24 can all be positioned very close to a suture securing device held between tines 6. The ends of elongate member 2, suture clamping means 8 and suture recovery means 15 which are operated by the surgeon outside the body of the patient may be provided with textured surfaces or any other means to facilitate easy handling.

In the embodiment as shown in FIGS. 12, 14, 15 and 16, the apparatus may be provided without integral suture recovery means and/or suture clamping means. If provided without such means, the suture may be threaded about the device using suitable conventional surgical instruments. If provided with such means, preferably the holding member, suture recovery means and suture clamping means are supplied as an integral unit capable of insertion down a single port for endoscopic surgery.

The suture securing apparatus may be made from any suitable materials by any suitable method. Preferably elongate member 2, suture clamping means 8 and shaft 14 are made from surgical steel which can be sterilized and re-used a number of times. Suture loading member 20 may be disposable and made from a suitable sterilizable polymeric material. The loading loop may be any suitable flexible wire, filament or the like. Preferably when a disposable suture loading member is used and the loading loop is to be separable, the loading loop is made from a narrow gauge suture material or the like.

It will be appreciated that various modifications, additions and/or alterations may be made to the apparatus previously described without departing from the ambit of the present invention.

I claim:

1. A suture securing apparatus for positioning a suture securing device having a passage therethrough, the apparatus comprising:
   (i) a holding member having at one end a handle and at the other end means for engaging the suture securing device;
   (ii) suture recovery means, slidably associated with said holding means, for drawing a loop of suture through the passage in the suture securing device, said suture recovery means including a snare passable through the passage of the suture securing device and retractable through the passage such that when said snare is passed through the passage and a portion of suture is snared, the snare may be retracted through the passage bringing with it a loop of the suture, said snare being a loop of filament; and
   (iii) suture clamping means, associated with said holding means, for securely engaging suture which has been passed through the loop in said suture securing device.

2. A suture securing apparatus according to claim 1 wherein said snare is attached to a member removably connectable to a retractable shaft, and said snare is at least partially severable from said member when said shaft is retracted along said apparatus such that the snare is disengageable from the loop of suture recovered through the passage when the shaft is retracted along said apparatus.

3. A suture securing apparatus for positioning a suture securing device having a passage therethrough, the apparatus comprising:
   (i) a holding member having at one end a handle and at the other end means for engaging the suture securing device;
   (ii) suture recovery means, slidably associated with said holding member, for drawing a loop of suture through the passage in the suture securing device, said suture recovery means including a snare passable through the passage of the suture securing device and retractable through the passage such that when said snare is passed through the passage and a portion of suture is snared, the snare maybe retracted through the passage bring with it a loop of the suture; and
   (iii) suture clamping means, associated with said holding means, for securely engaging suture which has been passed through the loop in said suture securing device, said suture clamping means comprising two members, one member having a loop with an abutment portion and the other member having a tongue adapted to bear upon the abutment portion such that when a suture is passed through the loop, the tongue may be pressed against the suture to hold it securely between the tongue and the abutment portion.

4. A suture securing apparatus for positioning a suture securing device having a passage therethrough, the apparatus comprising:
   (i) a holding member having at one end a handle and at the other end means for engaging the suture securing device, said means for engaging including a plurality of tines having projecting portions releasably engaging corresponding portions on the device;
   (ii) suture recovery means, slidably associated with said holding member, for drawing a loop of suture through the passage in the suture securing device; and
   (iii) suture clamping means, associated with said holding member, for securely engaging suture which has been passed through the loop in said suture securing device.

5. A suture securing apparatus according to claim 4 wherein said tines are resiliently biased toward a device holding position.

6. A suture securing apparatus according to claim 4 wherein said suture clamping means comprises two members, one member having a loop with an abutment portion and the other member having a tongue adapted to bear upon the abutment portion such that when a suture is passed through the loop, the tongue may be pressed against the suture to hold it securely between the tongue and the abutment portion.

7. A suture securing apparatus according to claim 4 wherein the holding member has an axis and said clamping means is retractable along said axis.

8. A suture securing apparatus according to claim 4 wherein said suture clamping means and said suture recovery means and locatable within an axial bore along said holding member.

9. A suture securing apparatus according to claim 4 wherein at least one of said suture recovery means and said suture clamping means may be actuated in the region of said handle.

10. A method of securing a suture at a desired surgical site comprising:
    (a) providing a suture securing device consisting of a surgically implantable body having a tissue abutting side and a suture loop side, and a passage through said body having openings adjacent said tissue abutting side and said suture loop side;
    (b) providing a suture securing apparatus having;
       (i) a holding a member having at one end a handle and at the other end means for engaging said suture securing device;
       (ii) suture recovery means adapted to draw a loop of suture through said passage in said suture securing device; and
       (iii) suture clamping means adapted to securely engage suture which has been passed through the loop in said suture securing device;
    (c) engaging said suture securing device with said holding member;
    (d) passing said suture recovery means through said passage from said suture loop side to said tissue abutting side and snaring the suture to be secured;
    (e) drawing a loop of suture through said passage with said suture recovery means to leave a free end of suture on the tissue abutting side of said device;
    (f) passing said free end of suture about said body, through said loop of suture and clamping in said suture clamping means; and
    (g) manipulating said suture securing device to the desired surgical site and retracting said clamping means to draw said suture taut about said suture securing device.

11. A method according to claim 10 further including the steps of:

(h) retracting said suture recovery means to disengage said suture loop; and (i) retracting said holding member to disengage said suture securing device.

12. A suture securing apparatus for postioning a suture securing device having a passage therethrough, the apparatus comprising:

(i) a holding member having at one end a handle and at the other end means for engaging the suture securing device;

(ii) suture recovery means, slidably associated with said holding member, for drawing a loop of suture through the passage in the suture securing device, said suture recovery means including a snare passable through the passage of the suture securing device and retractable through the passage such that when said snare is passed through the passage and a portion of suture is snared, the snare may be retracted through the passage bringing with it a loop of the suture;

(iii) said snare being attached to a member removably connectable to a retractable shaft, and said snare being at least partially severable from said member when said shaft is retracted along said apparatus such that the snare is disengageable from the loop of suture recovered through the passage when the shaft is retracted along said apparatus; and (iv) suture clamping means, associated with said holding means, for securely engaging suture which has been passed through the loop in said suture securing device.

13. A suture securing apparatus for positioning a suture securing device having a passage therethrough, the apparatus comprising:

(i) a holding member that includes a plurality spaced tines that are movable together and apart to selectively grasp and release said suture securing device;

(ii) a suture recovery member, slidably associated with said holding member, for drawing a loop of suture through the passage in the suture securing device, said suture recovery member including a snare passable through the passage of the suture securing device and retractable through the passage such that when said snare is passed through the passage and a portion of suture is snared, the snare may be retracted through the passage bringing with it a loop of the suture; and (iii) a suture clamp, associated with said holding member, for securely engaging suture which has been passed through the loop of suture that has been retracted through the passage in said suture securing device.

14. A suture securing apparatus according to claim 13 wherein the holding member has an axis and said suture clamp is retractable along said axis.

15. A suture securing apparatus according to claim 13 wherein said holding member has a distal end at which said tines are disposed and a proximal end, said suture recovery member being coupled to said proximal end to allow said suture recovery member to be actuated to retract said snare through the passage in the suture securing device.

16. A suture securing apparatus according to claim 13 wherein said holding member has a distal end at which said tines are disposed and a proximal end, said suture clamp being coupled to said proximal end to allow said suture clamp to be actuated to securely engage suture that has been passed through the loop of suture.

17. A suture securing apparatus according to claim 16 wherein said holding member has a distal end at which said tines are disposed and a proximal end, said suture clamp being coupled to said proximal end to allow said suture clamp to be actuated to retract said suture clamp along an axis of said holding member.

18. A suture securing apparatus according to claim 13 further comprising an actuator positioned to engage said tines and move said tines apart to release said suture securing device from said holding member.

19. A suture securing apparatus for positioning a suture securing device having a passage therethrough, the apparatus comprising:

(i) a holding member having at a first end a handle and a second end configured to selectively grasp the suture securing device at said second end and release said suture securing device;

(ii) a suture recovery member, slidably associated with said holding member, for drawing a loop of suture through the passage in the suture securing device, said suture recovery member including a snare passage through the passage of the suture securing device and retractable through the passage such that when said snare is passed through the passage and a portion of suture is snared, the snare may be retracted through the passage bringing with it a loop of the suture; and (iii) a suture clamp, associated with said holding member, for securely engaging suture which has been passed through the loop of suture that has been retracted through the passage in said suture securing device, said suture clamp and said suture recovery member being disposed within an axial bore along said holding member.

20. A suture securing apparatus for positioning a suture securing device having a passage therethrough, the apparatus comprising:

a holding member having at one end a handle and at the other end at least two tines for engaging the suture securing device, such tine having a projecting portion adapted to releasably engage a corresponding portion on the device;

an inner surface of each tine including a cam; and a ram slidably associated with said holding member for slidably engaging the tine cams to force said projecting portions of said tines apart to disengage the suture securing device within a patient.

21. A suture securing apparatus according to claim 20 wherein said tines are resiliently biased toward one another to engage the suture securing device.

22. A suture securing apparatus according to claim 20 wherein said cams includes grooves which receive said ridges.

* * * * *

UNITED STATES PATENT AND TRADEMARK OFFICE
CERTIFICATE OF CORRECTION

PATENT NO. : 5,741,281

DATED : April 21, 1998

INVENTOR(S) : Christopher Martin

It is certified that error appears in the above-identified patent and that said Letters Patent is hereby corrected as shown below:

Col. 1, line 29, replace "anaesthesis" with -- anaesthesia --.

Col. 1, line 34, replace "cholecystactomy" with -- cholecystectomy --.

Col. 3, line 51, replace "came" with --cams--.

Col. 4, line 30, replace "elongated" with --elongate--.

Col. 4, line 55, replace "camp" with --cams--.

Col. 6, line 10, replace "opening" with --operating--.

Col. 6, line 48, after "holding" insert --means--.

Col. 6, line 67, replace "14" with --16--.

Col. 7, claim 3, line 53, replace "bring" with --bringing--.

Col. 8, claim 4, line 4, after "portions" insert --for--.

UNITED STATES PATENT AND TRADEMARK OFFICE
CERTIFICATE OF CORRECTION

PATENT NO. : 5,741,281

DATED : April 21, 1998

INVENTOR(S) : Christopher Martin

It is certified that error appears in the above-identified patent and that said Letters Patent is hereby corrected as shown below:

Col. 10, claim 19, line 26, replace "passage" with --passable--.

Col. 10, claim 20, line 45, replace "such" with --each--.

Col. 10, claim 22, line 57, after "includes" insert --ridges on said inner surfaces, and said ram includes--.

Signed and Sealed this

Twenty-seventh Day of April, 1999

Attest:

Q. TODD DICKINSON

Attesting Officer

Acting Commissioner of Patents and Trademarks